United States Patent
Shaw (10) Patent No.: US 10,309,280 B2
(45) Date of Patent: Jun. 4, 2019

(54) GAS INTRODUCTION FOR UREA SOLUTION FREEZE PROTECTION

(71) Applicant: Continental Automotive Systems, Inc., Auburn Hills, MI (US)

(72) Inventor: Keith Aaron Shaw, Yorktown, VA (US)

(73) Assignee: Continental Powertrain USA, LLC, Auburn Hills, MI (US)

(*) Notice: Subject to any disclaimer, the term of this patent is extended or adjusted under 35 U.S.C. 154(b) by 637 days.

(21) Appl. No.: 14/940,528

(22) Filed: Nov. 13, 2015

(65) Prior Publication Data
US 2017/0138239 A1 May 18, 2017

(51) Int. Cl.
*F01N 3/20* (2006.01)
*C07C 273/02* (2006.01)
*B01D 53/94* (2006.01)

(52) U.S. Cl.
CPC .......... *F01N 3/2066* (2013.01); *C07C 273/02* (2013.01); *B01D 53/9431* (2013.01); *B01D 2251/2067* (2013.01); *F01N 2610/08* (2013.01)

(58) Field of Classification Search
CPC .. F01N 3/2066; F01N 2610/08; C07C 273/02
See application file for complete search history.

(56) References Cited

U.S. PATENT DOCUMENTS

| | | | |
|---|---|---|---|
| 9,010,089 B2 | 4/2015 | Bugos et al. | |
| 2009/0025373 A1 | 1/2009 | Buerglin | |
| 2011/0162351 A1 | 7/2011 | Yano | |
| 2013/0042598 A1* | 2/2013 | Bugos | F01N 3/2066 60/274 |
| 2014/0196808 A1 | 7/2014 | Besnard | |

FOREIGN PATENT DOCUMENTS

| | | |
|---|---|---|
| DE | 102008054726 A1 | 6/2010 |
| DE | 102010030923 A1 | 1/2012 |
| EP | 2134939 B1 | 6/2012 |
| JP | 2009530536 A | 8/2009 |
| JP | 2010077902 A | 4/2010 |
| JP | 2014037788 A | 2/2014 |
| JP | 2014531551 A | 11/2014 |

(Continued)

OTHER PUBLICATIONS

Urea Solution "AdBlue," Achema.*

(Continued)

*Primary Examiner* — Audrey K Bradley (57) ABSTRACT

A selective catalytic reduction solution having urea, water and gas bubbles contained within the solution. In particular, the solution has a urea content that is present in an amount greater than 31% (m/m) mass fraction of material and gas bubbles in the solution in an amount between about 7% to about 9% of the volume of solution when the solution is at a pressure of about 1 bar absolute. When the selective catalytic reduction solution is pressurized to a range between 6 bar and 7.5 bar, the gas bubbles are in a range between about 1.33% to about 1.07% of the solution when the solution is pressurized. The presence of the gas bubbles provides an expansion volume for the urea solution, if the urea solution begins freezing due to cold temperatures.

14 Claims, 6 Drawing Sheets

(56) References Cited

FOREIGN PATENT DOCUMENTS

| KR | 101556330 | 10/2015 | | |
|---|---|---|---|---|
| KR | 101556330 B1 * | 10/2015 | | |
| WO | WO-2005005799 A1 * | 1/2005 | ............. | B01D 53/90 |

OTHER PUBLICATIONS

Korean Notice of Allowance dated Jan. 5, 2018 for counterpart Korean patent application No. 10-2016-0099682.
Japan Office Action dated Oct. 30, 2017 for counterpart Japan patent application 2016-220541.
Koren Office Action dated Sep. 1, 2017 for corresponding Korean patent application 10-2016-0099682.
Chinese Office Action dated Nov. 2, 2018 for counterpart Chinese patent application 201610534700.8.

* cited by examiner

GAS INTRODUCTION FOR UREA SOLUTION FREEZE PROTECTION

FIELD OF THE INVENTION

The present invention relates to a freeze protected selective catalytic reduction solution and use in connection with a reductant delivery unit.

BACKGROUND OF THE INVENTION

Recent legislation in Europe and North America has been imposing more stringent exhaust emissions requirements for vehicles. In particular, there have been new mandates for lean-burn technologies for compression ignition (diesel) engines, as well as direct injection engines that must operate under lean and ultra-lean conditions. Lean burn engines exhibit high levels of nitrogen oxide (NOx) emissions that are difficult to treat in oxygen-rich exhaust environments characteristic of lean-burn combustion. Exhaust after treatment technologies are currently being developed that will treat NOx under these conditions. One of the technologies comprises a catalyst that facilitates the reactions of ammonia ($NH_3$) with the exhaust nitrogen oxides (NOx) to produce nitrogen (N) and water ($H_2O$). This technology is referred to as selective catalytic reduction (SCR).

However, one of the obstacles is that ammonia ($NH_3$) is difficult to handle in its pure form in the automotive environment; therefore, systems have been developed that use a liquid aqueous urea solution, typically at 32% concentration of urea ($CO(NH_2)_2$). The solution is referred to as AUS-32, also known under its commercial name of AdBlue®. The urea solution is delivered to the hot exhaust stream of a vehicle and is transformed into ammonia in the exhaust after undergoing thermolysis or thermodecomposition into ammonia and isocyanic acid (HNCO). The isocyanic acid then undergoes a hydrolysis with water present in the exhaust and is transformed into ammonia and carbon dioxide ($CO_2$). The ammonia resulting from the thermolysis and hydrolysis then undergoes a catalyzed reaction with nitrogen oxides as described previously.

One of the obstacles with using a urea solution is that the current guidelines for AUS-32 contain a mixture of urea with water, which means that the solution is subject to freezing, typically at minus 11° C. This prevents an obstacle with SCR technologies because there is a substantial concern about the freezing of the solution which can cause expansion and blocking of the reductant delivery unit (RDU) that delivers the urea solution to the exhaust system. If the solution freezes within the RDU, the whole RDU can become clogged or have components such as hoses, injection heads, tanks, pumps and other components break due to the expansion of the frozen solution.

In order to address the freezing concerns, several different types of purge systems have been developed where the solution supply line and injection head of the RDU are purged upon turning off the vehicle engine, so that the components will have very little if any solution within, thereby helping to eliminate the potential for damage or blockage due to freezing of the solution. Additionally, there have been other developments where heaters are placed within the solution supply tank and heat tape is used along the solution supply line to ensure that the solution supply line remains warm and does not allow the solution to freeze. However, these solutions rely upon providing power to the RDU system components in order to heat the components when the vehicle is sitting with the engine off. If the vehicle is stored for a long period of time in cold weather such systems can cause an unwanted drain on the vehicle's battery or require a separate power source. It is therefore desirable to develop more practical freeze protection for SCR systems in order to protect the components of the RDU.

SUMMARY OF THE INVENTION

The present invention relates to a selective catalytic reduction (SCR) solution having urea, water and gas bubbles contained within the solution. In particular, the solution has a urea content that is present in an amount greater than 31% (m/m) mass fraction of material and gas bubbles in the solution in an amount between about 7% to about 9% of the volume of solution when the solution is at a pressure of about 1 bar absolute. When the selective catalytic reduction solution is pressurized to a range between 6 bar and 7.5 bar, the gas bubbles are in a range between about 1.33% to about 1.07% of the solution when the solution is pressurized. The presence of the gas bubbles in the selective catalytic reduction solution will help to prevent freezing of the components of the RDU because the gas bubbles occupy a small volume of the solution when the solution is pressurized, but when the vehicle is turned off, the reduction delivery unit will be depressurized and the gas bubbles will occupy a larger volume of the solution contained within the reduction delivery unit. The presence of the gas bubbles provides an expansion volume for the urea solution if the SCR solution begins freezing due to cold temperatures. Therefore, the components of the RDU and other system components including the supply lines to the RDU, supply tank, and pump will all be protected from freezing by gas bubbles in the SCR solution itself, thereby eliminating the need to purge or heat the RDU system.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

In the following examples the volume of the gas bubbles in the SCR solution for a given temperature and pressure is calculated using the ideal gas law, which has the equation PV=nRT where P is pressure, V is volume, n is the number of moles, R is the gas constant and T is temperature. The number of moles and gas constant are cancelled out when determining the volume of a gas between its pressurized and depressurized state. Determining the volume of gas bubbles in a pressurized state is accomplished using the equation (P1)(V1)/T1=(P2)(V2)/T2, where P1 is pressure of the pressurized SCR solution. T1 varies but most extreme scenario is maximum allowable fluid temperature inside the injector in operating mode, which currently is 130 C (403 K). P2 is pressure after depressurization and is 1 bar absolute. V2 will vary depending on the desired volume of gas bubbles after depressurization, however, a range between about 7% to about 10%, generally about 7% to about 9% and ideally 8% are all desirable volumes depending on particular application. T2 is the freezing point of the SCR solution, which in the case of AdBlue® is minus 11 C (262 K). Determining the volume of the gas bubbles in SCR solution when pressurized (i.e., V1) is accomplished with the formula V1=(P2)(V2)(T1)/(P1)(T2). Using the above formulas the following samples were created as set forth in the Examples below.

EXAMPLES

Several different samples of a selective catalytic reduction (SCR) solution are created having urea, water and gas bubbles as the main components. Unless otherwise indicated, the unit m/m as used herein refers to mass fraction of material. The table below sets forth the general characteristics of the SCR solution, which includes a number of various elements and compounds that are present within the solution and will be collectively referred to herein as "additional elements and compounds".

TABLE 1

Urea-water Solution Characteristics

| Characteristics | Unit | Limits Min. | Limits Max. |
|---|---|---|---|
| Urea content[a] | % (m/m)[d] | 31.8 | 33.2 |
| Density at 20° C.[c] | kg/m³ | 1087.0 | 1093.0 |
| Refractive index at 20° C.[c] | — | 1.3814 | 1.3843 |
| Alkalinity as NH₃ | % (m/m)[d] | — | 0.2 |
| Biuret | % (m/m)[d] | — | 0.3 |
| Aldehydes | mg/kg | — | 5 |
| Insoluble matter | mg/kg | — | 20 |
| Phosphate (PO₄) | mg/kg | — | 0.5 |
| Calcium | mg/kg | — | 0.5 |
| Iron | mg/kg | — | 0.5 |
| Copper | mg/kg | — | 0.2 |
| Zinc | mg/kg | — | 0.2 |

TABLE 1-continued

Urea-water Solution Characteristics

| Characteristics | Unit | Limits Min. | Limits Max. |
|---|---|---|---|
| Chromium | mg/kg | — | 0.2 |
| Nickel | mg/kg | — | 0.2 |
| Aluminum | mg/kg | — | 0.5 |
| Magnesium | mg/kg | — | 0.5 |
| Sodium | mg/kg | — | 0.5 |
| Potassium | mg/kg | — | 0.5 |

* The term "(m/m)" is used to represent the mass fraction of material

As shown in the table above and also included in the samples below, a typical SCR solution prepared in accordance with this invention contains some additional elements and compounds in small quantities such as NH3 (between 0% m/m and 0.2% m/m), Biuret (between 0% m/m and 0.2% m/m), Aldehydes (less than or equal to about 5 mg/kg), insoluable matter (less than or equal to about 20 mg/kg), phosphate (less than or equal to about 0.5 mg/kg), calcium (less than or equal to about 0.5 mg/kg), iron (less than or equal to about 0.5 mg/kg), copper (less than or equal to about 0.2 mg/kg), zinc (less than or equal to about 0.2 mg/kg), chromium (less than or equal to about 0.2 mg/kg), nickel (less than or equal to about 0.2 mg/kg), aluminum (less than or equal to about 0.5 mg/kg), magnesium (less than or equal to about 0.5 mg/kg), sodium (less than or equal to about 0.5 mg/kg) and potassium (less than or equal to about 0.5 mg/kg).

In the examples below SCR solution, also referred to as a liquid solution is prepared by first preparing a liquid solution and then gas bubbles are added to each of the liquid solution samples to create a infused SCR solution. The gas bubbles are prepared and introduced by several sources including pressurized gas canisters of air or carbon dioxide, aerating the solutions with a pump connected to an air source, where bubbles are mixed with solution moving through a pump or by agitation where the liquid solution is agitated causing air bubbles to mix into the solution in combination with a pump for pressurizing moving the agitated solution.

Example 1

A first group of infused SCR solution samples are prepared by mixing a liquid solution with a urea content of generally greater than about 31% m/m with water less than or equal to about 69% and the above described additional elements and compounds making up the remainder of the samples of the group. Gas bubbles or dissolved gas are introduced to each of the liquid solution samples to create a infused selective catalytic reduction (SCR) solution prepared at a temperature of 262 Kalvin (K) and a pressure of about 1 bar absolute. The volume of the mixture of liquid solution and gas bubbles at a pressure of 1 bar absolute in one sample contains gas bubbles greater than about 7% of the total volume of solution including the liquid solution and gas bubbles. Further samples of the first group are prepared by introducing gas bubbles between about 7% of the total volume of infused SCR solution (including liquid solution and gas bubbles) to about 9% of the total volume of infused SCR solution (including liquid solution and gas bubbles) at a pressure of about 1 bar absolute. Additional infused SCR solution samples are prepared with gas bubbles in each sample being about 7.25,%, about 7.5%, about 7.75%, about 8%, about 8.25,%, about 8.5% and about 8.75% of the total volume of infused SCR solution (including the liquid solution and gas bubbles) all at a pressure of about 1 bar absolute and at a temperature of about 262 K. Additional infused SCR solution samples are prepared with gas bubbles of each sample being greater than about 9%, about 9.25%, about 9.5%, about 9.75% and about 10% of the total volume of the infused SCR solution (including the liquid solution and gas bubbles) all at pressure of about 1 bar absolute and at a temperature of about 262 K.

Further samples are prepared where the infused SCR solution samples were prepared under a pressure of at least about 6 bar, a temperature of 262 K, yielding gas bubbles of each sample that are about 1.33% of the total volume of the infused SCR solution (including the liquid solution and gas bubbles) at a temperature of 262K and a pressure of at least about 6 bar. Other samples was prepared at a pressure of at least about 6 bar, temperature of less than or equal to 403 K yielding gas bubbles in the infused SCR solution that are less than or equal to about 2.05% total volume of infused SCR solution (including the liquid solution and gas bubbles).

Further infused SCR solution samples were prepared at a pressure of at least about 7 bar, temperature of 262 K yielding gas bubbles in the infused SCR solution that are about 1.14% total volume of infused SCR solution (including the liquid solution and gas bubbles) and a second group mixed at a pressure of about 7 bar, temperature of less than or equal to 403K yielding gas bubbles in the infused SCR solution that are less than or equal to about 1.76% total volume of infused SCR solution (including the liquid solution and gas bubbles). Further samples were prepared at a pressure of at least about 7.5 bar, temperature of 262 K yielding gas bubbles in the infused SCR solution that are about 1.07% total volume of infused SCR solution (including the liquid solution and gas bubbles) and a second group mixed at a pressure of about 7.5 bar, temperature of less than or equal to 403 K yielding gas bubbles in the infused SCR solution that are less than or equal to about 1.64% total volume of infused SCR solution (including the liquid solution and gas bubbles).

Further samples were prepared at a pressure of at least about 8 bar, temperature of 262 K yielding gas bubbles in the infused SCR solution that are about 1.00% total volume of infused SCR solution (including the liquid solution and gas bubbles) and a second group mixed at a pressure of about 8 bar, temperature of less than or equal to 403 K yielding gas bubbles in the infused SCR solution that are less than or equal to about 1.54% total volume of infused SCR solution (including the liquid solution and gas bubbles). Further samples were prepared at a pressure of at least about 3 bar, temperature of 262 K yielding gas bubbles in the infused SCR solution that are about 2.67% total volume of infused SCR solution (including the liquid solution and gas bubbles) and a second group mixed at a pressure of about 3 bar, temperature of less than or equal to 403 K yielding gas bubbles in the infused SCR solution that are less than or equal to about 4.10% total volume of infused SCR solution (including the liquid solution and gas bubbles).

Further samples were prepared at a pressure of at least about 10 bar, temperature of 262 K yielding gas bubbles in the infused SCR solution that are about 0.080% total volume of infused SCR solution (including the liquid solution and gas bubbles) and a second group mixed at a pressure of about 10 bar, temperature of less than or equal to 403 K yielding gas bubbles in the infused SCR solution that are less than or equal to about 1.23% total volume of infused SCR solution (including the liquid solution and gas bubbles).

Further samples are also prepared where the liquid solution and gas bubbles (SCR solution are mixed under a pressure at numerous increments in a range of about 3 bar to about 10 bar at a temperature of less than or equal to about 403 K and the gas bubbles of each sample are less than or equal to about 4.10% of the total volume of SCR solution to greater than or equal to about 1.23% of the total volume of the infused SCR solution (including the liquid solution and gas bubbles under pressure).

Example 2

A second group of infused SCR solution samples are prepared by first mixing liquid solution samples having a urea content range between about 31% m/m to about 34% m/m with water content range between about 69% m/m to about 66% m/m, urea of about 31% m/m to about 33% m/m with water content range between about 69% m/m to about 67% m/m, urea of about 31% m/m to about 32% m/m with water content range between about 69% m/m to about 68% m/m, urea of about 32% m/m to about 34% m/m with water content range between about 68% m/m to about 66% m/m, urea of about 33% m/m to about 34% m/m with water content range between about 67% m/m to about 66% m/m, urea of about 31% m/m to about 33% m/m with water content range between about 69% m/m to about 67% m/m, urea of about 32% m/m to about 33% m/m with water content range between about 68% m/m to about 67% m/m, urea of about 31% m/m to about 32% m/m with water content range between about 69% m/m to about 68% m/m and the above described additional elements and compounds making up the remaining contents of the samples of the group.

Gas bubbles or dissolved gas are introduced to each of the liquid solution samples to create a infused selective catalytic reduction (SCR) solution prepared at a temperature of 262 Kalvin (K) and a pressure of about 1 bar absolute. The volume of the mixture of liquid solution and gas bubbles at a pressure of 1 bar absolute in one sample contains gas bubbles greater than about 7% of the total volume of solution including the liquid solution and gas bubbles. Further samples of the first group are prepared by introducing gas bubbles between about 7% of the total volume of infused SCR solution (including liquid solution and gas bubbles) to about 9% of the total volume of infused SCR solution (including liquid solution and gas bubbles) at a pressure of about 1 bar absolute. Additional infused SCR solution samples are prepared with gas bubbles in each sample being about 7.25,%, about 7.5%, about 7.75%, about 8%, about 8.25,%, about 8.5% and about 8.75% of the total volume of infused SCR solution (including the liquid solution and gas bubbles) all at a pressure of about 1 bar absolute and at a temperature of about 262 K. Additional infused SCR solution samples are prepared with gas bubbles of each sample being greater than about 9%, about 9.25%, about 9.5%, about 9.75% and about 10% of the total volume of the infused SCR solution (including the liquid solution and gas bubbles) all at pressure of about 1 bar absolute and at a temperature of about 262 K.

Further samples are prepared where the infused SCR solution samples were prepared under a pressure of at least about 6 bar, a temperature of 262 K, yielding gas bubbles of each sample that are about 1.33% of the total volume of the infused SCR solution (including the liquid solution and gas bubbles) at a temperature of 262K and a pressure of at least about 6 bar. Other samples was prepared at a pressure of at least about 6 bar, temperature of less than or equal to 403 K yielding gas bubbles in the infused SCR solution that are less than or equal to about 2.05% total volume of infused SCR solution (including the liquid solution and gas bubbles).

Further infused SCR solution samples were prepared at a pressure of at least about 7 bar, temperature of 262 K yielding gas bubbles in the infused SCR solution that are about 1.14% total volume of infused SCR solution (including the liquid solution and gas bubbles) and a second group mixed at a pressure of about 7 bar, temperature of less than or equal to 403K yielding gas bubbles in the infused SCR solution that are less than or equal to about 1.76% total volume of infused SCR solution (including the liquid solution and gas bubbles). Further samples were prepared at a pressure of at least about 7.5 bar, temperature of 262 K yielding gas bubbles in the infused SCR solution that are about 1.07% total volume of infused SCR solution (including the liquid solution and gas bubbles) and a second group mixed at a pressure of about 7.5 bar, temperature of less than or equal to 403 K yielding gas bubbles in the infused SCR solution that are less than or equal to about 1.64% total volume of infused SCR solution (including the liquid solution and gas bubbles).

Further samples were prepared at a pressure of at least about 8 bar, temperature of 262 K yielding gas bubbles in the infused SCR solution that are about 1.00% total volume of infused SCR solution (including the liquid solution and gas bubbles) and a second group mixed at a pressure of about 8 bar, temperature of less than or equal to 403 K yielding gas bubbles in the infused SCR solution that are less than or equal to about 1.54% total volume of infused SCR solution (including the liquid solution and gas bubbles). Further samples were prepared at a pressure of at least about 3 bar, temperature of 262 K yielding gas bubbles in the infused SCR solution that are about 2.67% total volume of infused SCR solution (including the liquid solution and gas bubbles) and a second group mixed at a pressure of about 3 bar, temperature of less than or equal to 403 K yielding gas bubbles in the infused SCR solution that are less than or equal to about 4.10% total volume of infused SCR solution (including the liquid solution and gas bubbles).

Further samples were prepared at a pressure of at least about 10 bar, temperature of 262 K yielding gas bubbles in the infused SCR solution that are about 0.080% total volume of infused SCR solution (including the liquid solution and gas bubbles) and a second group mixed at a pressure of about 10 bar, temperature of less than or equal to 403 K yielding gas bubbles in the infused SCR solution that are less than or equal to about 1.23% total volume of infused SCR solution (including the liquid solution and gas bubbles).

Further samples are also prepared where the liquid solution and gas bubbles (SCR solution are mixed under a pressure at numerous increments in a range of about 3 bar to about 10 bar at a temperature of less than or equal to about 403 K and the gas bubbles of each sample are less than or equal to about 4.10% of the total volume of SCR solution to greater than or equal to about 1.23% of the total volume of the infused SCR solution (including the liquid solution and gas bubbles under pressure).

Example 3

A third group of SCR solution samples are prepared by first mixing liquid solution samples having a urea content of about 32.5% m/m with water in about 67.5% m/m and the above described additional elements and compounds making up the remainder of the samples of the group.

Gas bubbles or dissolved gas are introduced to each of the liquid solution samples to create a infused selective catalytic reduction (SCR) solution prepared at a temperature of 262 Kalvin (K) and a pressure of about 1 bar absolute. The volume of the mixture of liquid solution and gas bubbles at a pressure of 1 bar absolute in one sample contains gas bubbles greater than about 7% of the total volume of solution including the liquid solution and gas bubbles. Further samples of the first group are prepared by introducing gas bubbles between about 7% of the total volume of infused SCR solution (including liquid solution and gas bubbles) to about 9% of the total volume of infused SCR solution (including liquid solution and gas bubbles) at a pressure of about 1 bar absolute. Additional infused SCR solution samples are prepared with gas bubbles in each sample being about 7.25,%, about 7.5%, about 7.75%, about 8%, about 8.25,%, about 8.5% and about 8.75% of the total volume of infused SCR solution (including the liquid solution and gas bubbles) all at a pressure of about 1 bar absolute and at a temperature of about 262 K. Additional infused SCR solution samples are prepared with gas bubbles of each sample being greater than about 9%, about 9.25%, about 9.5%, about 9.75% and about 10% of the total volume of the infused SCR solution (including the liquid solution and gas bubbles) all at pressure of about 1 bar absolute and at a temperature of about 262 K.

Further samples are prepared where the infused SCR solution samples were prepared under a pressure of at least about 6 bar, a temperature of 262 K, yielding gas bubbles of each sample that are about 1.33% of the total volume of the infused SCR solution (including the liquid solution and gas bubbles) at a temperature of 262K and a pressure of at least about 6 bar. Other samples was prepared at a pressure of at least about 6 bar, temperature of less than or equal to 403 K yielding gas bubbles in the infused SCR solution that are less than or equal to about 2.05% total volume of infused SCR solution (including the liquid solution and gas bubbles).

Further infused SCR solution samples were prepared at a pressure of at least about 7 bar, temperature of 262 K yielding gas bubbles in the infused SCR solution that are about 1.14% total volume of infused SCR solution (including the liquid solution and gas bubbles) and a second group mixed at a pressure of about 7 bar, temperature of less than or equal to 403K yielding gas bubbles in the infused SCR solution that are less than or equal to about 1.76% total volume of infused SCR solution (including the liquid solution and gas bubbles). Further samples were prepared at a pressure of at least about 7.5 bar, temperature of 262 K yielding gas bubbles in the infused SCR solution that are about 1.07% total volume of infused SCR solution (including the liquid solution and gas bubbles) and a second group mixed at a pressure of about 7.5 bar, temperature of less than or equal to 403 K yielding gas bubbles in the infused SCR solution that are less than or equal to about 1.64% total volume of infused SCR solution (including the liquid solution and gas bubbles).

Further samples were prepared at a pressure of at least about 8 bar, temperature of 262 K yielding gas bubbles in the infused SCR solution that are about 1.00% total volume of infused SCR solution (including the liquid solution and gas bubbles) and a second group mixed at a pressure of about 8 bar, temperature of less than or equal to 403 K yielding gas bubbles in the infused SCR solution that are less than or equal to about 1.54% total volume of infused SCR solution (including the liquid solution and gas bubbles). Further samples were prepared at a pressure of at least about 3 bar, temperature of 262 K yielding gas bubbles in the infused SCR solution that are about 2.67% total volume of infused SCR solution (including the liquid solution and gas bubbles) and a second group mixed at a pressure of about 3 bar, temperature of less than or equal to 403 K yielding gas bubbles in the infused SCR solution that are less than or equal to about 4.10% total volume of infused SCR solution (including the liquid solution and gas bubbles).

Further samples were prepared at a pressure of at least about 10 bar, temperature of 262 K yielding gas bubbles in the infused SCR solution that are about 0.080% total volume of infused SCR solution (including the liquid solution and gas bubbles) and a second group mixed at a pressure of about 10 bar, temperature of less than or equal to 403 K yielding gas bubbles in the infused SCR solution that are less than or equal to about 1.23% total volume of infused SCR solution (including the liquid solution and gas bubbles).

Further samples are also prepared where the liquid solution and gas bubbles (SCR solution are mixed under a pressure at numerous increments in a range of about 3 bar to about 10 bar at a temperature of less than or equal to about 403 K and the gas bubbles of each sample are less than or equal to about 4.10% of the total volume of SCR solution to greater than or equal to about 1.23% of the total volume of the infused SCR solution (including the liquid solution and gas bubbles under pressure).

Figure 1:
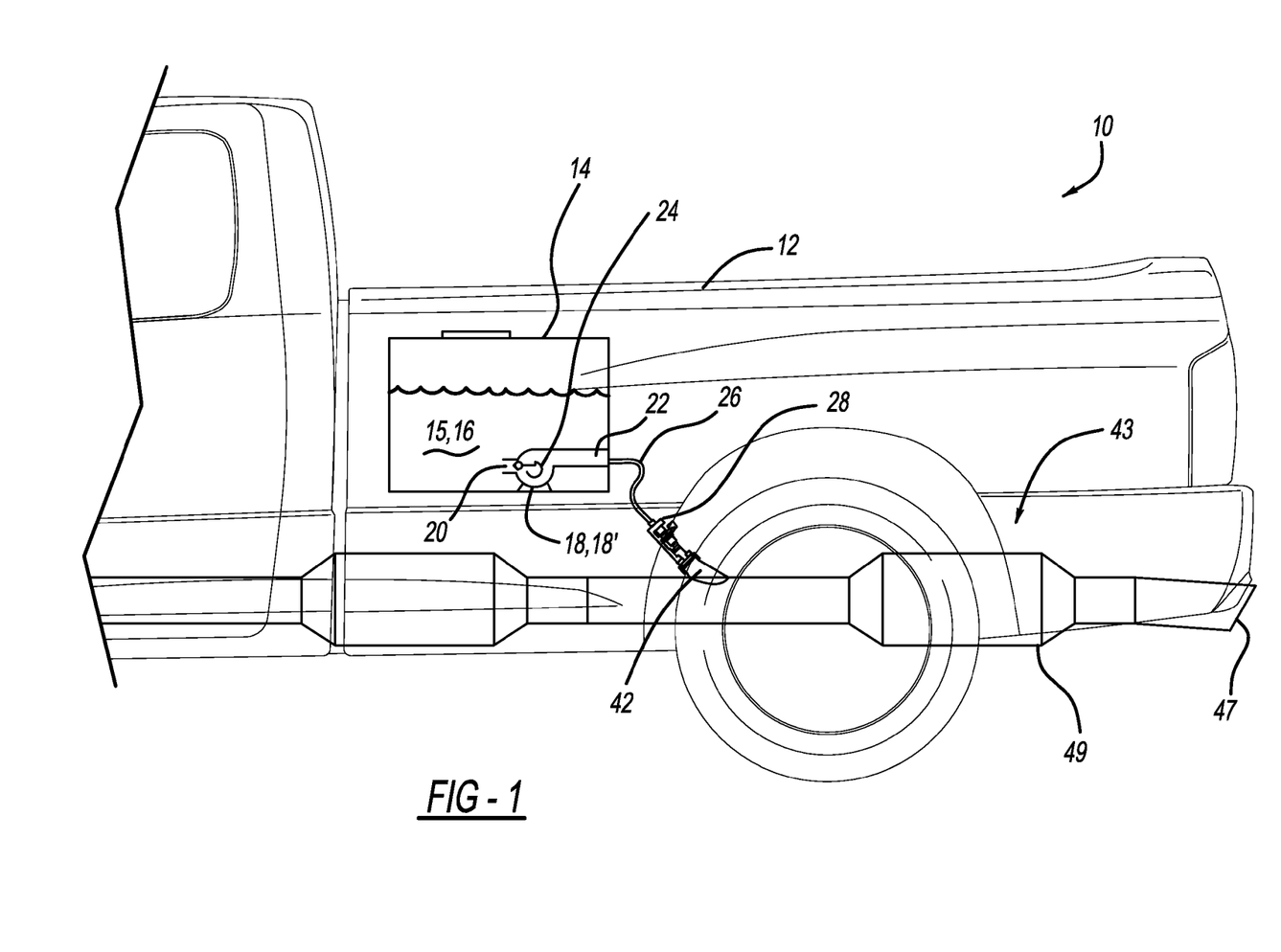
FIG. 1 is a schematic diagram of a reductant delivery unit for a vehicle exhaust system.

The prepared infused SCR solution samples set forth in the above examples are then used in a selective catalytic reduction (SCR) system on a vehicle. Referring now to FIG. 1 there is a schematic diagram of a SCR system 10 for use on a vehicle 12. The SCR system 10 has a supply tank 14 for holding a liquid solution set out in the above Examples prior to introducing the gas bubbles or for holding a infused infused SCR solution 16 prepared according to the EXAMPLE 1, EXAMPLE 2 and EXAMPLE 3 above.

Located in the supply tank 14 is a pump 18, 18' that is submersed in the SCR solution 15 or infused infused SCR solution 16. The pump 18, 18' has a solution inlet 20 and a pump element 24 that creates a suction at the solution inlet 20, then pumps the infused infused SCR solution 16 or SCR liquid solution 15 to a pump outlet 22. The pump element 24 is any type of suitable component capable of moving the liquid solution 15 or infused SCR solution 16 and can include, but is not limited to a vane pump element, impeller pump element, piston pump element and a diaphragm element.

An outlet 22 of the pump 18 is connected to a hose 26 that extends from the supply tank 14 to a reductant delivery unit 28. The SCR solution 15 or infused SCR solution 16 exits the outlet 22 into the hose 26. Where infused SCR solution 16 is pumped through the hose 26, the hose 26 is made of polypropylene or some other less expensive material because the use of the infused SCR solution 16 with gas bubbles will allow space for freezing and prevent cracking of the hose 26.

Figure 2A:
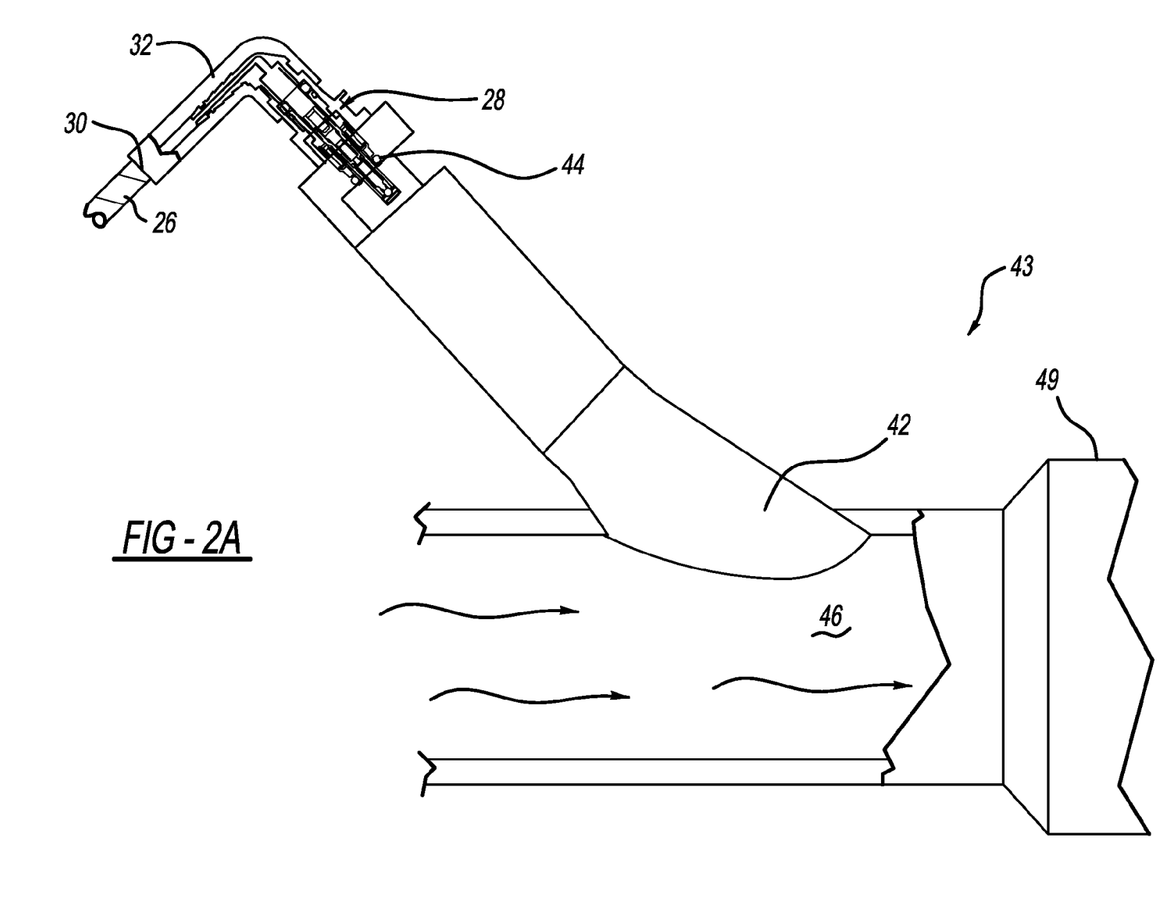
FIG. 2A is a partial cross-section view of an injection head and supply hose for a reductant delivery unit connected to a portion of a vehicle exhaust system.
Figure 2B:
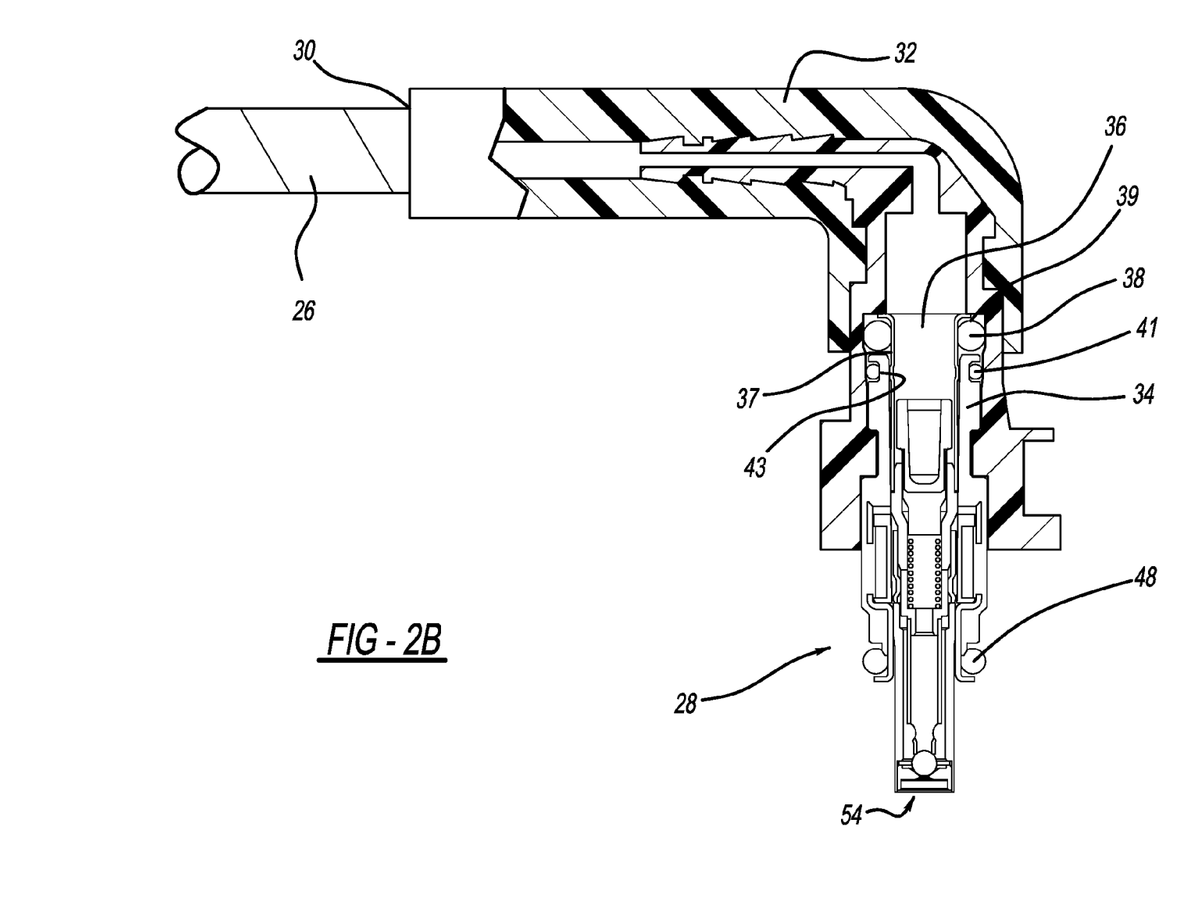
FIG. 2B is a cross-sectional side plan view of the injection head and a portion of the supply hose for a reductant delivery unit.
Figures 3, 4:
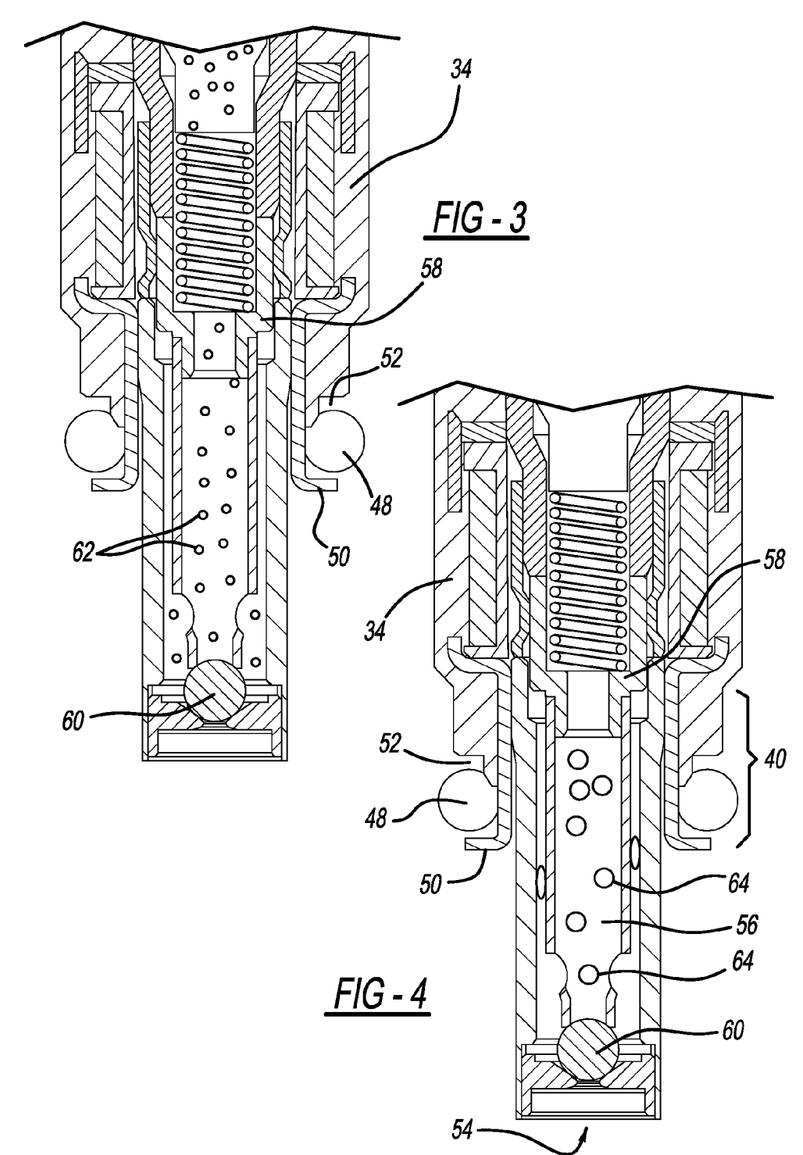
FIG. 3 is magnified cross-sectional side view of a portion of the injection head with pressurized solution.
FIG. 4 is magnified cross-sectional side view of a portion of the injection head with depressurized solution.
Figure 5:
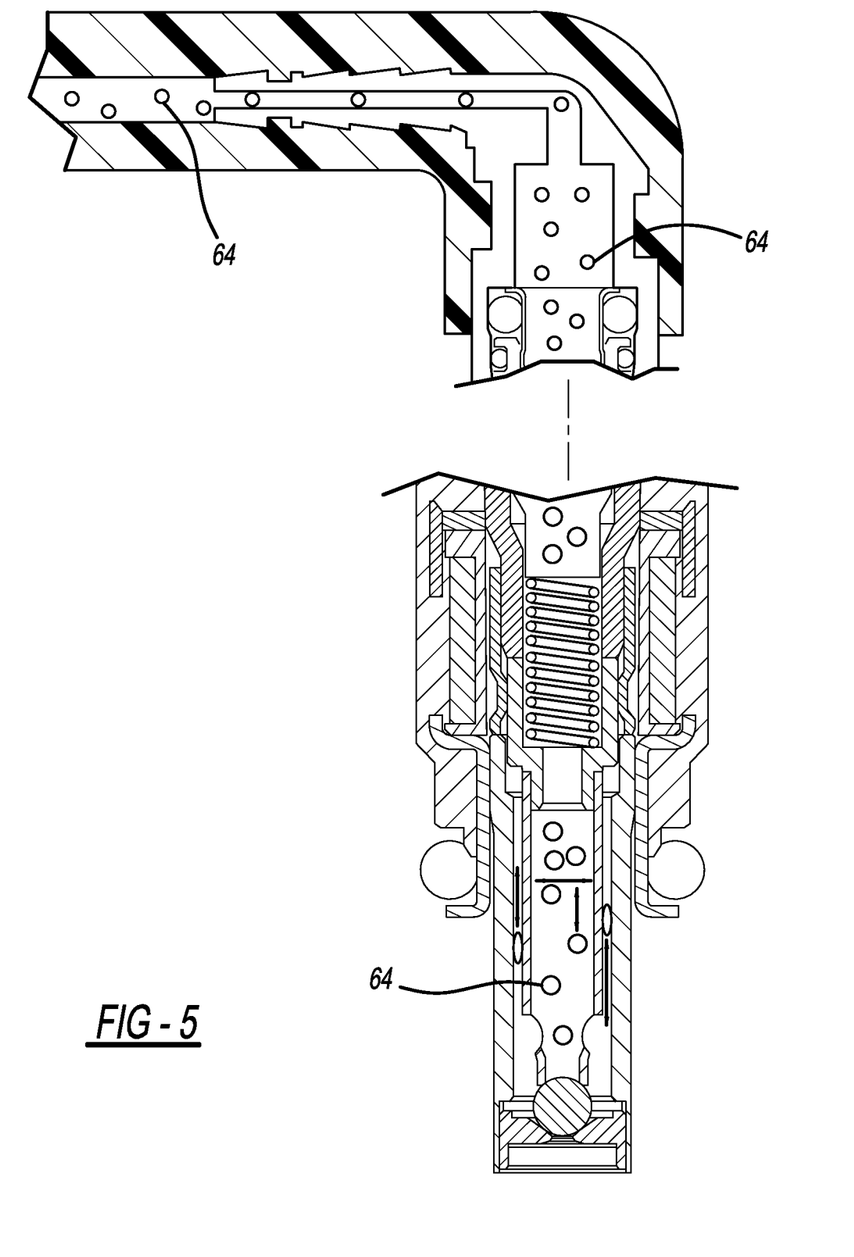
FIG. 5 is magnified cross-sectional side view of a portion of the injection head and a portion of the supply hose with depressurized solution undergoing freezing.

Referring also to FIGS. 2A and 2B show an end 30 of the hose 26 that is connected to a connector 32 which connects to the reductant delivery unit 28. Referring also to FIG. 3-5 the reductant delivery unit 28 has a body 34 with an inlet 36 that receives infused SCR solution 16 from the hose 26 though the connector 32. A sealed connection between the connector 32 and the body 34 of the RDU 28 is provided by an upper seal 38 and middle seal 41. The upper seal 38 is positioned in an upper groove 39 formed by a flange 37 piece and an upper end of the body 34. The middle seal 41 is positioned in a middle groove 43 formed by a reduced diameter portion on the body 34. The upper seal 38 and middle seal 41 are disposed about a portion of the body 34 of the RDU 28 and create two sealing points between the connector 32 and the body 34, thereby preventing the leaking of infused SCR solution 16 from an area between the body 34 and the connector 32. While an upper seal 38 and middle seal 41 are shown and described it is within the scope of this invention for a greater or lesser number of seals to be provided.

The body 34 of the RDU 28 has a mounting region 40 that engagingly slides into an aperture 44 formed in a decomposition tube 42, that connects to an exhaust flow path 46 in an exhaust pipe 47. In on embodiment of the invention the exhaust flow path 46 connects to the vehicle exhaust system 43 upstream of a catalytic converter 49 that connects to an exhaust pipe 47 in the vehicle exhaust system 43 shown in FIG. 1. As shown in FIG. 4, a gasket or seal 48 is disposed between a step or groove 52 formed in a downstream end of body 34 and a downstream end of an injector flange 50 of the RDU 28. Gasket 48 is configured to be sandwiched between injector flange 50 and an inner mounting surface which defines aperture 44 of decomposition tube 42 when the body 34 of the RDU 28 is disposed in aperture 44 (best seen in FIG. 2A).

The body 34 of the RDU 28 has an outlet 54 that extends into the decomposition tube 42. The body 34 of the RDU 28 has a fluid passage 56 extending between the inlet 36 and outlet 54, where the infused SCR solution 16 flows through the RDU 28. During operation of the vehicle 12 the SCR system 10 is activated and the pump 18 draws in liquid solution 15 or infused SCR solution 16 from the supply tank 14 and pumps the infused SCR solution 16 into the hose 26. The infused SCR solution 16 contained within the hose 26 and RDU 28 is pressurized by the pump 18. When the pressurized infused SCR solution 16 enters the RDU 28 the solution will flow into the fluid passage 56 where a spring-loaded piston valve 58 and ball valve 60 are positioned within the fluid passage 56, so that when the infused SCR solution 16 is pressurized the infused SCR solution 16 will selectively pass through the fluid passage 56, past the spring-loaded piston valve 58 and the ball valve 60, thereby spraying solution through the outlet 54. When the vehicle 12 is turned off the pump 18 of the SCR system 10 will also be turned off and the SCR system 10 will be depressurized, which causes the spring-loaded piston valve 58 and ball valve 60 to move to a closed position to prevent infused SCR solution 16 from leaking out of the outlet 54. The pressure of the infused SCR solution 16 within the RDU 28 and hose 26 will be relieved and the anti-freeze benefits of the infused SCR solution 16 will be described below.

Referring now to FIGS. 3-5, the effects of the pressurization and depressurization of the gas bubbles within the infused SCR solution 16 is shown. In accordance with the present invention FIG. 3 shows the infused SCR solution 16 in its pressurized form where gas bubbles 62 are condensed due to the pressure of the infused SCR solution 16 resulting from pressure build up caused by the pump 18. Pressurized bubbles 62 take up about 1% to about 2% of the infused SCR solution 16 when pressurized; however, the volume will vary depending on the temperature and pressure in the system. Using the equation described in the Example above the actual volume can be calculated.

When the vehicle 12 is turned off and the SCR system 10 is depressurized to a pressure of about 1 bar absolute, the compressed gas bubbles 62 become decompressed gas bubbles 64, as shown in FIGS. 4 and 5. The decompressed gas bubbles 64 are much larger and create airspace volume that is greater than about 6% of the infused SCR solution 16. FIG. 5 shows the RDU unit 28 when the infused SCR solution 16 begins to freeze, which typically occurs at about minus 11° C. The decompressed gas bubbles 64 expand to accommodate the freezing liquid of the liquid portions of the infused SCR solution 16. A similar result can be seen in the hose 26 as shown in FIG. 5 when depressurized bubbles 64 in infused SCR solution 16 are also present.

Figure 6:
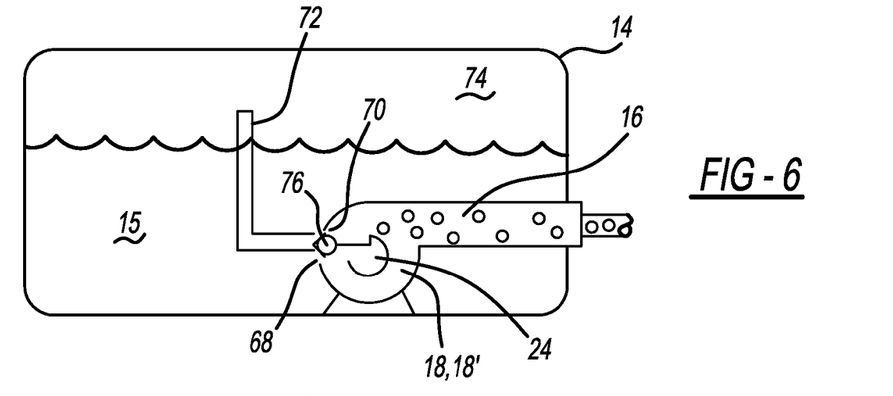
FIG. 6 is a schematic diagram of a solution supply tank with pump and a method of introducing gas bubbles into the urea solution.
Figure 7:
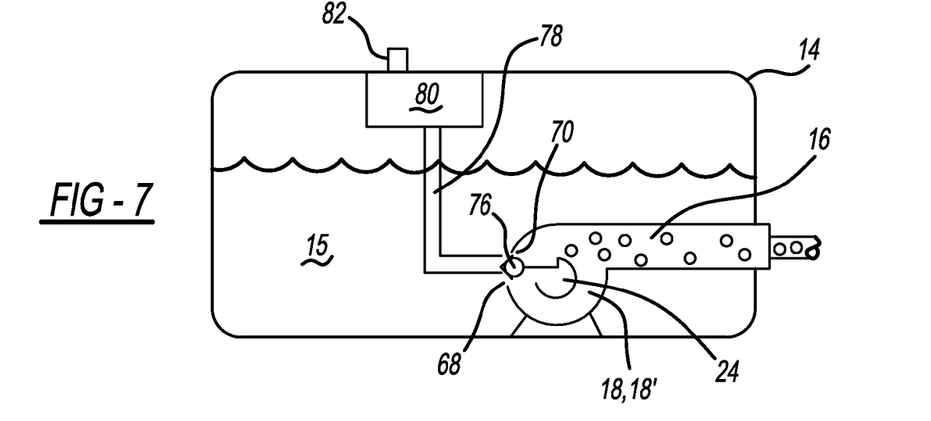
FIG. 7 is a schematic diagram of a solution supply tank with pump and an alternate method of introducing gas bubbles into the urea solution.
Figure 8:
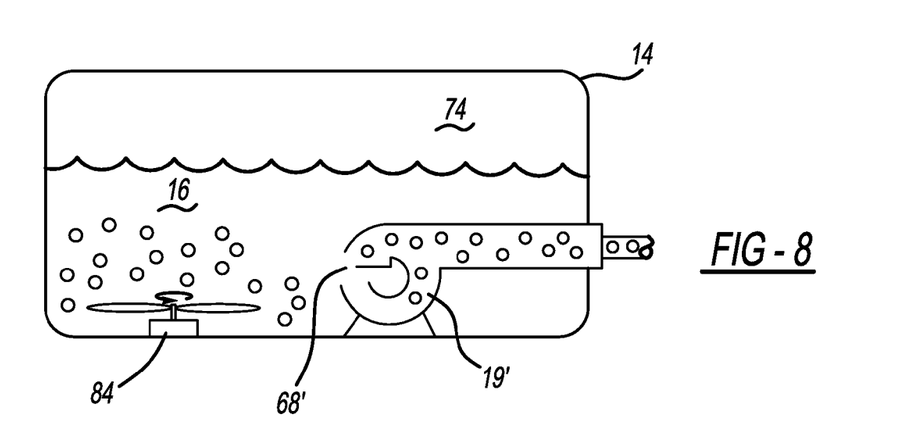
FIG. 8 is a schematic diagram of a solution supply tank with pump and an alternate method of introducing gas bubbles into the urea solution.

FIGS. 6-8 demonstrate three different alternate embodiments for introducing gas bubbles into the samples of liquid solution 15 in order to create the infused SCR solution 16 in accordance with the present invention. Referring now to FIG. 6 the supply tank 14 contains the liquid solution 15, with a pump element 24 that has a liquid inlet 68 for receiving liquid solution and an air inlet 70 that is connected to a snorkel 72 that extends to the headspace in the supply tank 14, which is located above the fluid level of the liquid solution 15. The snorkel 72 draws in air from the headspace 74 into the pump element 24 of the pump 14 through the air inlet 70. The air from the headspace 74 enters the air inlet 70 by flowing past a ball valve 76 where the air is mixed with the liquid solution 15 to create bubbles to make up the infused SCR solution 16 that pass through the pump outlet in accordance with the present invention.

Referring now to FIG. 7 a second embodiment of the invention is shown where the supply tank 14 has liquid solution 15 and a submerged pump 18 located within the liquid solution 15. The pump 18, like the pump in FIG. 6 has a liquid inlet 68 and an air inlet 70. However, the air inlet 70 is connected to a gas hose 78 that extends to a compressed gas canister 80 containing a pressurized gas such as carbon dioxide, air or oxygen. A controller 82 is connected to the compressed gas canister to control the amount of gas that flows from the compressed gas canister 80 into the gas hose 78. The compressed gas will flow past the ball valve 76 and enter the pump 18 through the air inlet 70. The pump element 24 of the pump 18 will mix the gas coming in through the air inlet 70 with the liquid solution 15 entering through the liquid inlet 68 in the proper amount in order to create the infused SCR solution 16 in accordance with the present invention.

Referring now to FIG. 8 a third embodiment of the invention is shown where the supply tank 14 has infused SCR solution 16 created within the supply tank 14. In this embodiment of the invention an agitator 84, which is shown as a fan or movable pump number causes the infused SCR solution 16 within the supply tank 14 to mix and become turbulent so that air from the headspace 74 of the supply tank 14 mixes within the infused SCR solution 16 and forms gas bubbles in the infused SCR solution 16. The present embodiment of the invention has a pump 18' with a single liquid inlet 68' that draws in the infused SCR solution 16.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A reductant delivery unit with a freeze prevention selective catalytic reduction solution comprising:
   an exhaust system having a selective catalytic reduction portion where a mist of a solution containing urea, water and gas bubbles is mixed with exhaust gas from the exhaust system;
   a tank containing a solution of urea and water and including an air space above the solution;
   a device disposed at least partly within the tank and configured to selectively generate a pressurized solution of urea, water and air bubbles at an outlet of the device, the device comprising a compressed gas canister in fluid communication with a pressurization pump, the outlet of the device being an outlet of the pressurization pump;
   an injection head connected to the selective catalytic reduction portion for introducing the mist;
   a selectively pressurized solution supply line connected between the outlet of the device and the injection head, said pressurized solution supply line contains the solution of urea, water and gas bubbles, where the solution is present in the selectively pressurized solution supply line in a pressurized state and a depressurized state, where the gas bubbles are smaller and have less volume when the solution is in the pressurized state and the gas bubbles are larger and have greater volume when the solution is in the depressurized state, thereby creating freezing air space when the solution is depressurized; and
   a pressure relief valve connected to the supply line for causing solution to transition between the pressurized state and the depressurized state by relieving the pressurized state of the solution in the solution supply line, the pressure relief valve forming an injector of the reductant delivery unit with the injection head, the injection head being downstream of the relief valve, relative of flow of the solution through the pressure relief valve and the injection head, the pressure relief valve opening and closing based upon an amount of pressure in the pressurized solution supply line without being controlled by a controller.

2. The reductant delivery unit of claim 1 wherein said solution has a urea content of one selected from the group consisting of: greater than 31% (m/m) mass fraction of material, a range between 31% mass fraction of material to 34% (m/m) mass fraction of material, and 32.5% (m/m) mass fraction of material.

3. The reductant delivery unit of claim 1 wherein the gas bubbles are present in said solution at a pressure of one bar absolute and in an amount being one selected from the group consisting of between 7% and 9% of the volume of the solution, and between 9% and 10% of the volume of the solution.

4. The reductant delivery unit of claim 1 wherein at a temperature of the solution of 262 K and a pressure of the solution of at least three bar, the gas bubbles are present in said solution in an amount being between 2.67% and 0.080% of the volume of the solution.

5. The reductant delivery unit of claim 1 wherein at a temperature of the solution of 262 K and a pressure of the solution of at least ten bar, the gas bubbles are present in said solution in an amount being 0.080% of the volume of the solution.

6. The reductant delivery unit of claim 1 wherein the gas bubbles, are in an amount being one selected from the group consisting of: between 7% and 10% of the volume of the solution at a temperature of 262 K and a pressure of 1 bar; between 1.23% and 0.080% of the volume of solution at a pressure of 10 bar and a temperature between 403 K and 262 K, respectively; and between 1.33% and 1.07% of the volume of solution at a temperature of 262 K and a pressure between 6 bar and 7.5 bar, respectively.

7. The reductant delivery unit of claim 1, further comprising a controller coupled to the compressed gas canister, the controller controlling an amount of gas that flows from the compressed gas canister to the pressurization pump.

8. A reductant delivery unit with a freeze prevention selective catalytic reduction solution for a vehicle having an exhaust flow path, comprising:
- an exhaust system having a selective catalytic reduction portion where a mist of a solution containing urea, water and gas bubbles is mixed with exhaust gas from the exhaust system;
- a tank containing a solution of urea and water and including an air space above the solution;
- a device disposed at least partly within the tank and configured to selectively generate a pressurized solution of urea, water and air bubbles at an outlet of the device, the device comprising a compressed gas canister in fluid communication with a pump, the outlet of the device being an outlet of the pump;
- a selectively pressurized solution supply line, in fluid communication with the outlet of the device, the supply line containing the solution of urea, water and gas bubbles, where the solution is present in the selectively pressurized solution supply line in a pressurized state and a depressurized state, where the gas bubbles are smaller and have less volume when the solution is in the pressurized state and the gas bubbles are larger and have greater volume when the solution is in the depressurized state, thereby creating freezing air space when the solution is depressurized;
- an injection head connected to the selective catalytic reduction portion for introducing the mist, said injection head is connectable to said supply line and receives said solution from said supply line, wherein said selectively pressurized solution is present in said injection head and has gas bubbles that limit the potential of ice to exert its blocking force on fluid path components of the injection head, wherein said injection head includes a flow path with an inlet and an outlet, a fluid flow path through a body of the injection head including an injector flange mounted to a metallic boss that is in communication with the vehicle's exhaust flow path, a gasket sandwiched between the injector flange and a mounting surface on the exhaust boss to permit the solution to pass from the outlet to the exhaust flow path; wherein the selectively pressurized solution contains gas bubbles that prevent the freezing of the solution that is contained within the body of the injection head;
- a pressure relief valve connected to the pressurized solution supply line for causing solution to transition between the pressurized state and the depressurized state by relieving the pressurized state of the solution in the solution supply line, the pressure relief valve forming an injector of the reductant delivery unit with the injection head, the injection head being downstream of the relief valve, relative to flow of the solution through the pressure relief valve and the injection head, the pressure relief valve opening and closing based upon an amount of pressure in the pressurized solution supply line without being controlled by a controller.

9. The reductant delivery unit of claim 8 wherein said solution has a urea content of one selected from the group consisting of greater than 31% (m/m) mass fraction of material, a range between 31% mass fraction of material to 34% (m/m) mass fraction of material, and 32.5% (m/m) mass fraction of material.

10. The reductant delivery unit of claim 8 wherein the gas bubbles are present in said solution at a pressure of one bar absolute and in an amount being one selected from the group consisting of between 7% and 9% of the volume of solution and between 9% and 10% of the volume of the solution.

11. The reductant delivery unit of claim 8 wherein at a temperature of the solution of 403 K and a pressure of the solution of at least three bar, the gas bubbles are present in said solution in an amount being between 1.23% and 4.10% of the volume of the solution.

12. The reductant delivery unit of claim 8 wherein at a temperature of the solution of 403 K and a pressure of the solution between 6 bar and 7.5 bar, the gas bubbles are present in said solution in an amount being between 2.05% and 1.64% of the volume of the solution.

13. The reductant delivery unit of claim 8 wherein the gas bubbles, when pressurized are in an amount being one selected from the group consisting of greater than 2.67% of the volume of the solution at a pressure less than or equal to three bar and a temperature of at least 262 K; between 2.67% and 0.080% of the volume of solution at a temperature of 262 K and a pressure between 3 bar and 10 bar, respectively; between 1.33% and 1.07% of the volume of solution at a temperature of 262 K and a pressure between 6 bar and 7.5 bar, respectively and greater than 0.080% of the volume of the solution at a pressure less than or equal to 10 bar and at a temperature of at least 262 K.

14. The reductant delivery unit of claim 8, further comprising a controller coupled to the compressed gas canister, the controller controlling an amount of gas that flows from the compressed gas canister to the pump.

\* \* \* \* \*